(12) United States Patent
Rege et al.

(10) Patent No.: US 10,646,426 B2
(45) Date of Patent: *May 12, 2020

(54) ORAL CARE COMPOSITIONS

(71) Applicant: Colgate-Palmolive Company, New York, NY (US)

(72) Inventors: Aarti Rege, East Windsor, NJ (US); Michael Prencipe, West Windsor, NJ (US); Marc Estriplet, Scotch Plains, NJ (US)

(73) Assignee: Colgate-Palmolive Company, New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/538,869

(22) Filed: Aug. 13, 2019

(65) Prior Publication Data

US 2019/0358141 A1 Nov. 28, 2019

Related U.S. Application Data

(63) Continuation of application No. 16/212,129, filed on Dec. 6, 2018, now Pat. No. 10,406,087, which is a continuation of application No. 15/674,034, filed on Aug. 10, 2017, now Pat. No. 10,179,098.

(60) Provisional application No. 62/437,085, filed on Dec. 21, 2016.

(51) Int. Cl.
| | | |
|---|---|---|
| *A61K 8/44* | (2006.01) |
| *A61K 8/21* | (2006.01) |
| *A61K 8/27* | (2006.01) |
| *A61K 8/365* | (2006.01) |
| *A61K 8/24* | (2006.01) |
| *A61Q 11/00* | (2006.01) |
| *A61K 8/362* | (2006.01) |

(52) U.S. Cl.
CPC ............. *A61K 8/44* (2013.01); *A61K 8/21* (2013.01); *A61K 8/24* (2013.01); *A61K 8/27* (2013.01); *A61K 8/362* (2013.01); *A61K 8/365* (2013.01); *A61Q 11/00* (2013.01)

(58) Field of Classification Search
CPC .................................................. A61K 8/44
See application file for complete search history.

(56) References Cited

U.S. PATENT DOCUMENTS

| | | |
|---|---|---|
| 2,876,166 A | 3/1959 | Nebergall |
| 4,961,924 A | 10/1990 | Suhonen |
| 5,188,820 A | 2/1993 | Cummins et al. |
| 6,045,800 A | 4/2000 | Kim et al. |
| 6,685,920 B2 | 2/2004 | Baig et al. |
| 6,696,045 B2 | 2/2004 | Yue et al. |
| 8,906,347 B2 | 12/2014 | Strand et al. |
| 9,968,803 B2 | 5/2018 | Fruge et al. |
| 2013/0209375 A1 | 8/2013 | Moya Argilagos et al. |
| 2013/0224270 A1 | 8/2013 | Robinson et al. |
| 2015/0305993 A1 | 10/2015 | Rege et al. |
| 2015/0313813 A1 | 11/2015 | Rege et al. |
| 2017/0319447 A1 | 11/2017 | Vemishetti et al. |
| 2017/0367947 A1 | 12/2017 | Rege et al. |

OTHER PUBLICATIONS

International Search Report and Written Opinion of the International Searching Authority in International Application No. PCT/US2017/046287, dated Oct. 30, 2017.

*Primary Examiner* — Benjamin J Packard

(57) ABSTRACT

An oral care composition comprising zinc phosphate, stannous fluoride, arginine or lysine and an organic acid buffer system, as well as methods of using the same.

11 Claims, No Drawings

ORAL CARE COMPOSITIONS

CROSS-REFERENCE TO RELATED PATENT APPLICATIONS

This application is a continuation of U.S. application Ser. No. 16/212,129, filed on Dec. 6, 2018, which is a continuation of U.S. application Ser. No. 15/674,034, filed on Aug. 10, 2017, now U.S. Pat. No. 10,179,098, which claims priority from U.S. Prov. Appl. No. 62/437,085, filed on Dec. 21, 2016, the contents of each of which are incorporated herein by reference in their entireties.

FIELD

The present invention relates to an oral care composition for use in the treatment or prevention of erosive tooth demineralization, gingivitis, plaque, and dental caries. This oral care composition includes zinc phosphate, stannous fluoride, arginine or lysine, and an organic acid buffer system.

BACKGROUND

Dental erosion involves demineralization and damage to the tooth structure due to acid attack from nonbacterial sources. Erosion is found initially in the enamel and, if unchecked, may proceed to the underlying dentin. Dental erosion may be caused or exacerbated by acidic foods and drinks, exposure to chlorinated swimming pool water, and regurgitation of gastric acids.

Dental plaque is a sticky biofilm or mass of bacteria that is commonly found between the teeth, along the gum line, and below the gum line margins. Dental plaque can give rise to dental caries and periodontal problems such as gingivitis and periodontitis. Dental caries tooth decay or tooth demineralization caused by acid produced from the bacterial degradation of fermentable sugar.

Oral care compositions which contain stannous ion sources exhibit excellent clinical benefits, particularly in the reduction of gingivitis and in the treatment or prevention of erosive tooth demineralization. Stannous fluoride is well known for use in clinical dentistry with a history of therapeutic benefits over forty years. However, until recently, its popularity has been limited by its instability in aqueous solutions. The instability of stannous fluoride in water is primarily due to the reactivity of the stannous ion ($Sn^{2+}$). Stannous salts readily hydrolyse above a pH of 4, resulting in precipitation from solution, with a consequent loss of the therapeutic properties.

One way to overcome the stability problems with stannous ions is to limit the amount of water in the composition to very low levels, or to use a dual phase system. Both of these solutions to the stannous ion problem have drawbacks. Low water oral care compositions can be difficult to formulate with desired rheological properties, and dual-phase compositions are considerably more expensive to manufacture and package.

Soluble zinc salts, such as zinc citrate, have been used in dentifrice compositions, but have several disadvantages. Zinc ions in solution impart an unpleasant, astringent mouthfeel, so formulations that provide effective levels of zinc, and also have acceptable organoleptic properties, have been difficult to achieve. Moreover, free zinc ions may react with fluoride ions to produce zinc fluoride, which is insoluble and so reduces the availability of both the zinc and the fluoride. Finally, the zinc ions will react with anionic surfactants such as sodium lauryl sulfate, thus interfering with foaming and cleaning.

Zinc phosphate ($Zn_3(PO_4)_2$) is insoluble in water, although soluble in acidic or basic solutions, e.g., solutions of mineral acids, acetic acid, ammonia, or alkali hydroxides. See, e.g., Merck Index, $13^{th}$ Ed. (2001) p. 1812, monograph number 10205. Partly because it is viewed in the art as a generally inert material, zinc phosphate is commonly used in dental cements, for example in cementation of inlays, crowns, bridges, and orthodontic appliances, which are intended to endure in the mouth for many years. Zinc phosphate dental cements are generally prepared by mixing zinc oxide and magnesium oxide powders with a liquid consisting principally of phosphoric acid, water, and buffers, so the cement comprising zinc phosphate is formed in situ by reaction with phosphoric acid.

Commercially available arginine-based toothpaste, for example, contains arginine bicarbonate and precipitated calcium carbonate, but not fluoride. The carbonate ion is believed to have cariostatic properties, and the calcium is believed to form a complex with arginine to provide a protective effect.

The formulation of certain oral care compositions presents special challenges. For example, oral care compositions comprising arginine or basic amino acids may have a basic pH, increasing potential for microbial contamination compared to acidic formulations. Moreover, not all preservatives are active at higher pH. Some preservatives negatively affect the taste or aesthetics of the product. While certain preservatives, such as ethanol or parabens, are known to be effective at a range of pHs, these preservatives are not suitable for all products or all markets.

Thus, there is a need for providing improved stannous ion containing products for treating or preventing erosion of tooth enamel with antimicrobial effectiveness, reducing plaque or treating or controlling gingivitis. There is also a desire for novel anti-microbial compositions that are stable in water and easy to manufacture.

BRIEF SUMMARY

Disclosed herein are high water oral care compositions comprising zinc phosphate, stannous fluoride, arginine or lysine, and an organic acid buffer system. Methods and uses for this composition are also described throughout. The compositions disclosed herein provide improved protection from demineralization and enhanced stannous stability compared to the prior art and certain market formulations, while also being able to afford the benefits derived from arginine or lysine. In some embodiments, the zinc phosphate is added to the dentifrice as a preformed salt. In some embodiments, the organic acid buffer system is a citric acid/citrate buffer system. In some embodiments, the oral care composition is a toothpaste or oral gel composition.

Further areas of applicability of the present disclosure will become apparent from the detailed description provided hereinafter. It should be understood that the detailed description and specific examples, while indicating the preferred embodiment of the disclosure, are intended for purposes of illustration only and are not intended to limit the scope of the disclosure.

DETAILED DESCRIPTION

The following description of the preferred embodiment(s) is merely exemplary in nature and is in no way intended to limit the disclosure, its application, or uses.

As used throughout, ranges are used as shorthand for describing each and every value that is within the range. Any value within the range can be selected as the terminus of the range. In addition, all references cited herein are hereby incorporated by reference in their entireties. In the event of a conflict in a definition in the present disclosure and that of a cited reference, the present disclosure controls.

Unless otherwise specified, all percentages and amounts expressed herein and elsewhere in the specification should be understood to refer to percentages by weight of the entire composition. The amounts given are based on the active weight of the material.

It has been surprisingly found that a high water oral care composition comprising zinc phosphate, stannous fluoride, and an organic acid buffer system, selected at certain concentrations and amounts, is unexpectedly more efficacious in boosting the anti-erosion and anti-microbial properties of a stannous ions containing formulation when compared to formulations according to the prior art.

As used herein, the term "high water" refers to an oral care composition, such as a toothpaste or oral gel, which comprises from 10% to 99% water, by weight of the composition. For example, the composition may comprise at least 10%, 15%, 20%, 25%, 30%, 35% or 40% water, up to a maximum of, for example, 60%, 70%, 80%, 90%, 95% or 99% water, by weight of the composition. As used herein, amounts of water refer to water added directly to the composition, as well as water added as part of ingredients or components which are added as aqueous solutions. In some embodiments, the composition comprises 10-60% water, or 10-50% water, or 10-40% water, or 10-30% water, or 15-30% water, or 20-30% water, or about 25% water, by weight of the composition.

As used herein, the term "preformed salt"—when used in reference to zinc phosphate—means that the zinc phosphate is not formed in situ in the oral care composition, e.g., through the reaction of phosphoric acid and another zinc salt.

In one aspect, the present disclosure therefore provides a high water oral care composition (Composition 1) comprising an orally acceptable carrier, zinc phosphate and stannous fluoride, arginine or lysine, and an organic acid buffer system. In further embodiments of this aspect, the present disclosure provides:

1.1 Composition 1, wherein the zinc phosphate is a preformed salt of zinc phosphate (e.g., zinc phosphate hydrate).

1.2 Composition 1 or 1.2, wherein the zinc phosphate is present in an amount sufficient so that the stannous fluoride dissociates to provide a therapeutically effective amount of stannous ions in aqueous solution.

1.3 Any preceding composition, wherein the amount of zinc phosphate is from 0.05 to 10% by weight, relative to the weight of the oral care composition, for example, from 0.1 to 8% by weight, or from 0.5 to 5% by weight, or from 0.5 to 4% by weight, or from 1 to 4%, or from 1 to 3% by weight, or from 2 to 3% by weight, or about 1% or about 2%, or about 2.25% or about 2.5%, by weight.

1.4 Any preceding composition, wherein the amount of the stannous fluoride is from 0.01% to 5% by weight, relative to the weight of the oral care composition, for example, from 0.05 to 4% by weight, or from 0.1% to 3% by weight, or from 0.2 to 2% by weight, or from 0.3 to 1% by weight, or from 0.4 to 0.8% by weight, or from 0.4 to 0.6% by weight, or from 0.4 to 0.5% by weight, or about 0.45% by weight (e.g., 0.454% by weight).

1.5 Any preceding composition, wherein the amount of the water is 10% by weight or more, relative to the weight of the oral care composition, for example, 10-90%, or 10-80%, or 10-70%, or 10-60%, or 10-50%, or 10-40%, or 10-30%, or 15-30%, or 20-30%, or about 18, or about 25%, by weight of the composition.

1.6 Any preceding composition, wherein the organic buffer system comprises a carboxylic acid and one or more conjugate base salts thereof, for example, alkali metal salts thereof.

1.7 Composition 1.6, wherein the acid is selected from citric acid, lactic acid, malic acid, maleic acid, fumaric acid, acetic acid, succinic acid, and tartaric acid.

1.8 Composition 1.6 or 1.7, wherein the one or more conjugate base salts are independently selected from sodium and potassium salts, or combinations thereof.

1.9 Composition 1.6, 1.7 or 1.8 wherein the acid is citric acid, and the one or more conjugate base salts comprise monosodium citrate (monobasic), disodium citrate (dibasic), trisodium citrate (tribasic), and combinations thereof.

1.10 Any preceding composition, wherein the composition comprises the organic acid buffer system in an amount of 0.1 to 5.0% by weight of the composition, measured as the combined amount of organic acid and any conjugate base salts; for example, from 0.5 to 4.0%, or from 1.0 to 3.0%, or from 1.5 to 3.0%, or from 1.0 to 2.4%, or from 1.0% to 2.0%, by weight of the composition.

1.11 Any preceding composition, wherein the buffer system consists of an organic acid and a conjugate base salt thereof, for example, in a ratio of from 1:1 to 1:10, e.g., from 1:2 to 1:8, or from 1:3 to 1:6, or from 1:4 to 1:6, or from 1:5 to 1:6, or about 1:5, by weight of the components.

1.12 Any preceding composition, wherein the buffer system comprises citric acid and a sodium citrate salt (e.g., trisodium citrate, disodium citrate, or monosodium citrate), in a ratio of from 1:3 to 1:6, or 1:4 to 1:6, or about 1:5 (e.g., about 1:5.7), by weight.

1.13 Any preceding composition, wherein the oral care composition further comprises an abrasive, for example, silica abrasives, calcium abrasives, and other abrasives as disclosed herein.

1.14 Any preceding composition, further comprising one or more humectants, as described herein, e.g., selected from sorbitol, glycerol, xylitol and propylene glycol, or combinations thereof.

1.15 Any preceding composition, further comprising one or more surfactants, as described herein, e.g., sodium lauryl sulfate, sodium laureth sulfate, or cocamidopropyl betaine, or combinations thereof.

1.16 Any preceding composition, further comprising an effective amount of one or more alkali phosphate salts for example orthophosphates, pyrophosphates, tripolyphosphates, tetraphosphates or higher polyphosphates.

1.17 Composition 1.16, wherein the alkali phosphate salts comprise tetrasodium pyrophosphate or tetrapotassium pyrophosphate, for example, in an amount of 0.5 to 5% by weight of the composition, e.g., 1-3%, or 1-2% or about 2% by weight.

1.18 Composition 1.16 or 1.17, wherein the alkali phosphate salts comprise sodium tripolyphosphate or potassium tripolyphosphate, for example, in an amount of 0.5 to 6% by weight of the composition, e.g., 1-4%, or 2-3% or about 3% by weight.

1.19 Any preceding composition, further comprising a whitening agent.

1.20 Any preceding composition, further comprising one or more sources of zinc ions in addition to the zinc phosphate, for example a zinc salt selected from zinc citrate, zinc oxide, zinc lactate, zinc pyrophosphate, zinc sulfate, or zinc chloride.

1.21 Any preceding composition, further comprising one or more fluoride ion sources in addition to the stannous fluoride, for example, a fluoride ion source selected from sodium fluoride, potassium fluoride, sodium monofluorophosphate, sodium fluorosilicate, ammonium fluorosilicate, amine fluoride, ammonium fluoride, and combinations thereof.

1.22 Any preceding composition, wherein the oral care composition is a dentifrice, e.g., a toothpaste or oral gel.

1.23 Any preceding composition, wherein the pH of the composition is from 6 to 9, such as from 6.5 to 8, or from 6.5 to 7.5, or about 7.0.

1.24 Any preceding composition, wherein the composition is a single-phase composition (e.g., not a dual-phase composition).

1.25 Any preceding composition, wherein the composition does not comprise one or more of zinc oxide, zinc citrate, or zinc lactate.

1.26 Any preceding composition, wherein the zinc phosphate is the only zinc ion source.

1.27 Any preceding composition, wherein the composition is essentially free or free of phosphates of more than four phosphate groups.

1.28 Any preceding composition, wherein the composition is essentially free or free of phosphates of more than three phosphate groups.

1.29 Any preceding composition, wherein the composition is essentially free or free of hexametaphosphate salts (e.g., sodium hexametaphosphate).

1.30 Any preceding composition, wherein the composition is free of methyl vinyl ether-maleic anhydride copolymer.

1.31 Any preceding composition, wherein the composition is free of anionic polymer.

1.32 Any of the preceding compositions, wherein the composition is effective upon application to the oral cavity, e.g., by rinsing, optionally in conjunction with brushing, to (i) reduce or inhibit formation of dental caries, (ii) reduce, repair or inhibit pre-carious lesions of the enamel, e.g., as detected by quantitative light-induced fluorescence (QLF) or electrical caries measurement (ECM), (iii) reduce or inhibit demineralization and promote remineralization of the teeth, (iv) reduce hypersensitivity of the teeth, (v) reduce or inhibit gingivitis, (vi) promote healing of sores or cuts in the mouth, (vii) reduce levels of acid producing bacteria, (viii) to increase relative levels of arginolytic bacteria, (ix) inhibit microbial biofilm formation in the oral cavity, (x) raise and/or maintain plaque pH at levels of at least pH 5.5 following sugar challenge, (xi) reduce plaque accumulation, (xii) treat, relieve or reduce dry mouth, (xiii) clean the teeth and oral cavity (xiv) reduce erosion, (xv) prevents stains and/or whiten teeth, (xvi) immunize the teeth against cariogenic bacteria; and/or (xvii) promote systemic health, including cardiovascular health, e.g., by reducing potential for systemic infection via the oral tissues.

1.33 Any of the preceding compositions where the arginine or lysine has the L-configuration (e.g., L-arginine).

1.34 Any of the preceding compositions comprising arginine in free form.

1.35 Any of the preceding compositions wherein the arginine or lysine is provided in the form of a di- or tri-peptide comprising arginine, or salts thereof.

1.36 Any of the preceding compositions wherein the basic amino acid is arginine, and wherein the arginine is present in an amount corresponding to 1% to 15%, e.g., 3 wt. % to 10 wt. % of the total composition weight, about e.g., 1.5%, 4%, 5%, or 8%, wherein the weight of the basic amino acid is calculated as free form.

1.37 Any of the preceding compositions wherein the amino acid is arginine from 0.1 wt. %-6.0 wt. %. (e.g., about 1.5 wt %).

1.38 Any of the preceding compositions wherein the amino acid is arginine from about 1.5 wt. %.

1.39 Any of the preceding compositions comprising lysine in free form.

1.40 Any of the preceding compositions wherein the basic amino acid is lysine, and wherein the lysine is present in an amount corresponding to 1% to 15%, e.g., 3 wt. % to 10 wt. % of the total composition weight, about e.g., 1.5%, 4%, 5%, or 8%, wherein the weight of the basic amino acid is calculated as free form.

1.41 Any of the preceding compositions wherein the amino acid is lysine from 0.1 wt. %-6.0 wt. %. (e.g., about 1.5 wt %).

1.42 Any of the preceding compositions wherein the amino acid is lysine from about 1.5 wt. %.

Any amount of zinc phosphate that is effective for protecting against enamel erosion and/or providing any of the other benefits described herein can be employed. Examples of suitable amounts of zinc phosphate can range from 0.05 to 5% by weight, such as from 0.1 to 4% by weight, or from 0.5 to 3% by weight, or from 0.5 to 2% by weight, or from 0.8 to 1.5% by weight, or from 0.9 to 1.1% by weight, or about 1% by weight, relative to the weight of the oral care composition.

While zinc phosphate is considered insoluble (e.g., poorly soluble), in water, when placed in formulation, e.g., at acidic or basic pH, zinc phosphate can dissolve sufficiently upon use to provide an effective concentration of zinc ions to the enamel, thereby protecting against erosion, reducing bacterial colonization and biofilm development, and providing enhanced shine to the teeth. It has also been discovered that zinc phosphate in a formulation with a second phosphate source enhances phosphate deposition. As explained in WO2014/088573, the disclosure of which is hereby incorporated by reference in its entirety, this is all unexpected, in view of the poor solubility of zinc phosphate, and the art-recognized view that it is substantially inert in conditions in the oral cavity, as evidenced by its widespread use in dental cement. At the same time, the formulations containing zinc phosphate do not exhibit the poor taste and mouthfeel, poor fluoride delivery, and poor foaming and cleaning associated with conventional zinc-based oral care products, which use more soluble zinc salts.

An amount of stannous fluoride, preferably an effective amount, is employed in combination with the zinc phosphate in the compositions of the present disclosure. For example, the stannous fluoride can be employed in an amount that is effective for providing anti-microbial benefits, such as anti-caries protection and/or anti-gingivitis protection, and/or anti-erosion benefits for protection of tooth enamel. Examples of suitable amounts of stannous fluoride range from 0.01% to 5% by weight, relative to the weight of the oral care composition, for example, from 0.05 to 4% by weight, or from 0.1% to 3% by weight, or from 0.2 to 2% by weight, or from 0.3 to 1% by weight, or from 0.4 to 0.8% by weight, or from 0.3 to 1% by weight, or from 0.4 to 0.5% by weight, or about 0.45% by weight (e.g., 0.454%), relative to the total weight of the dentifrice composition. Formulations can include stannous levels, provided by stannous fluoride, ranging for example, from 3,000 ppm to 15,000 ppm (mass fraction) stannous ions in the total composition. In embodiments, the soluble stannous content can range from 0.1 wt % to 0.5 wt %, or more, such as from 0.15 wt % to 0.32 wt %, based on the total weight of the composition.

The combination of zinc and stannous ions provides one or more of the following benefits: improved antimicrobial benefits compared to the zinc ions alone; improved control of plaque and/or gingivitis; improved protection against the erosion of tooth enamel.

In compositions comprising significant amounts of water, the zinc phosphate acts as a stabilizing agent for the stannous fluoride, so that the stannous fluoride remains in solution in the water. As discussed above, stannous fluoride is generally considered unstable in water due to the hydrolytic and oxidative loss of stannous ions at typical pH ranges employed in oral care compositions. Consequently, stannous fluoride is generally employed in compositions containing no water or low water, or with a chelating agent. Tedious procedures are employed in order to provide stable solutions in which the tendency of the stannous ion to be oxidized or hydrolyzed is inhibited. Applicants have surprisingly found that zinc phosphate and stannous fluoride can be combined together in a single phase formulation and stabilized by the presence of an appropriate organic acid buffer system. The organic acid buffer system helps solubilize the zinc phosphate and it helps stabilize the soluble stannous ions.

The compositions may optionally comprise additional ingredients suitable for use in oral care compositions. Examples of such ingredients include active agents, such as a fluoride source and/or a phosphate source in addition to zinc phosphate. The compositions may be formulated in a suitable dentifrice base, e.g., comprising abrasives, e.g., silica abrasives, surfactants, foaming agents, vitamins, polymers, enzymes, humectants, thickeners, additional antimicrobial agents, preservatives, flavorings, colorings, and/or combinations thereof. Examples of suitable dentifrice bases are known in the art. Alternatively, the compositions may be formulated as a gel (e.g., for use in a tray), chewing gum, lozenge or mint. Examples of suitable additional ingredients that can be employed in the compositions of the present disclosure are discussed in more detail below.

Active Agents:

The compositions of the disclosure may comprise various other agents that are active to protect and enhance the strength and integrity of the enamel and tooth structure and/or to reduce bacteria and associated tooth decay and/or gum disease or to provide other desired benefits. Effective concentration of the active ingredients used herein will depend on the particular agent and the delivery system used. The concentration will also depend on the exact salt or polymer selected. For example, where the active agent is provided in salt form, the counterion will affect the weight of the salt, so that if the counterion is heavier, more salt by weight will be required to provide the same concentration of active ion in the final product.

Compositions of the disclosure may contain from 0.1 to 1 wt % of an antibacterial agent, such as about 0.3 wt. %. Any suitable antimicrobial actives can be employed.

Basic Amino Acids

The basic amino acids which can be used in the compositions and methods of the invention include not only naturally occurring basic amino acids, such as arginine, lysine, and histidine, but also any basic amino acids having a carboxyl group and an amino group in the molecule, which are water-soluble and provide an aqueous solution with a pH of 7 or greater.

Accordingly, basic amino acids include, but are not limited to, arginine, lysine, serine, citrullene, ornithine, creatine, histidine, diaminobutanoic acid, diaminoproprionic acid, salts thereof or combinations thereof. In a particular embodiment, the basic amino acids are selected from arginine, citrullene, and ornithine.

In certain embodiments, the basic amino acid is arginine or lysine, for example, L-arginine, or a salt thereof.

The compositions of the invention are intended for topical use in the mouth and so salts for use in the present invention should be safe for such use, in the amounts and concentrations provided. Suitable salts include salts known in the art to be pharmaceutically acceptable salts are generally considered to be physiologically acceptable in the amounts and concentrations provided. Physiologically acceptable salts include those derived from pharmaceutically acceptable inorganic or organic acids or bases, for example acid addition salts formed by acids which form a physiological acceptable anion, e.g., hydrochloride or bromide salt, and base addition salts formed by bases which form a physiologically acceptable cation, for example those derived from alkali metals such as potassium and sodium or alkaline earth metals such as calcium and magnesium. Physiologically acceptable salts may be obtained using standard procedures known in the art, for example, by reacting a sufficiently basic compound such as an amine with a suitable acid affording a physiologically acceptable anion.

Fluoride Ion Source:

The oral care compositions can include one or more additional fluoride ion sources, e.g., soluble fluoride salts. A wide variety of fluoride ion-yielding materials can be employed as sources of soluble fluoride in the present compositions. Examples of suitable fluoride ion-yielding materials are found in U.S. Pat. No. 3,535,421, to Briner et al.; U.S. Pat. No. 4,885,155, to Parran, Jr. et al. and U.S. Pat. No. 3,678,154, to Widder et al, the disclosure of each of which is hereby incorporated by reference in their entirety. Representative fluoride ion sources include, but are not limited to, sodium fluoride, potassium fluoride, sodium monofluorophosphate, sodium fluorosilicate, ammonium fluorosilicate, amine fluoride, ammonium fluoride, and combinations thereof. In certain embodiments the fluoride ion source includes sodium fluoride, sodium monofluorophosphate as well as mixtures thereof. In certain embodiments, the oral care composition of the disclosure may contain stannous fluoride and any additional source of fluoride ions or fluorine-providing agents in amounts sufficient to supply, in total, from 25 ppm to 25,000 ppm (mass fraction) of fluoride ions, generally at least 500 ppm, e.g., from 500 to 2000 ppm, e.g., from 1000 to 1600 ppm, e.g., about 1450 ppm. The appropriate level of fluoride will depend on the particular application. A toothpaste for general consumer use would typically have from 1000 to about 1500 ppm, with pediatric toothpaste having somewhat less. A dentifrice or coating for professional application could have as much as 5,000 or even about 25,000 ppm fluoride. Additional fluoride ion sources may be added to the compositions of the disclosure at a level of from 0.01 wt. % to 10 wt. % in one embodiment or from 0.03 wt. % to 5 wt. %, and in another embodiment from 0.1 wt. % to 1 wt. % by weight of the composition. As discussed above, weights of fluoride salts to provide the appropriate level of fluoride ion will vary based on the weight of the counterion in the salt.

Abrasives:

The compositions of the disclosure can include abrasives. Examples of suitable abrasives include silica abrasives, such as standard cleaning silicas, high cleaning silicas or any other suitable abrasive silicas. Additional examples of abrasives that can be used in addition to or in place of the silica abrasives include, for example, a calcium phosphate abrasive, e.g., tricalcium phosphate ($Ca_3(PO_4)_2$), hydroxyapatite ($Ca_{10}(PO_4)_6(OH)_2$), or dicalcium phosphate dihydrate ($CaHPO_4.2H_2O$, also sometimes referred to herein as DiCal) or calcium pyrophosphate; calcium carbonate abrasive; or abrasives such as sodium metaphosphate, potassium metaphosphate, aluminum silicate, calcined alumina, bentonite or other siliceous materials, or combinations thereof.

Silica abrasive polishing materials useful herein, as well as the other abrasives, generally have an average particle size ranging between 0.1 and 30 microns, such as between 5 and 15 microns. The silica abrasives can be from precipitated silica or silica gels, such as the silica xerogels described in U.S. Pat. No. 3,538,230, to Pader et al. and U.S. Pat. No. 3,862,307, to Digiulio, the disclosures of which are incorporated herein by reference in their entireties. Particular silica xerogels are marketed under the trade name Syloid® by the W. R. Grace & Co., Davison Chemical Division. The precipitated silica materials include those marketed by the J. M. Huber Corp. under the trade name Zeodent®, including the silica carrying the designation Zeodent 115 and 119. These silica abrasives are described in U.S. Pat. No. 4,340,583, to Wason, the disclosure of which is incorporated herein by reference in its entirety. In certain embodiments, abrasive materials useful in the practice of the oral care compositions in accordance with the disclosure include silica gels and precipitated amorphous silica having an oil absorption value of less than 100 cc/100 g silica, such as from 45 cc/100 g to 70 cc/100 g silica. Oil absorption values are measured using the ASTA Rub-Out Method D281. In certain embodiments, the silicas are colloidal particles having an average particle size of from 3 microns to 12 microns, and from 5 to 10 microns. Examples of low oil absorption silica abrasives useful in the practice of the disclosure are marketed under the trade designation Sylodent XWA® by Davison Chemical Division of W.R. Grace & Co., Baltimore, Md. 21203. Sylodent 650 XWA®, a silica hydrogel composed of particles of colloidal silica having a water content of 29% by weight averaging from 7 to 10 microns in diameter, and an oil absorption of less than 70 cc/100 g of silica is an example of a low oil absorption silica abrasive useful in the practice of the present disclosure.

Any suitable amount of silica abrasive can be employed. Examples of suitable amounts include 10 wt. % or more dry weight of silica particles, such as from 15 wt. % to 30 wt. % or from 15 wt. % to 25 wt. %, based on the total weight of the composition.

Foaming Agents:

The oral care compositions of the disclosure also may include an agent to increase the amount of foam that is produced when the oral cavity is brushed. Illustrative examples of agents that increase the amount of foam include, but are not limited to polyoxyethylene and certain polymers including, but not limited to, alginate polymers.

The polyoxyethylene may increase the amount of foam and the thickness of the foam generated by the oral care compositions of the present disclosure. Polyoxyethylene is also commonly known as polyethylene glycol ("PEG") or polyethylene oxide. The polyoxyethylenes suitable for compositions of the present disclosure may have a molecular weight of from 200,000 to 7,000,000. In one embodiment the molecular weight may be from 600,000 to 2,000,000 and in another embodiment from 800,000 to 1,000,000. Polyox® is the trade name for the high molecular weight polyoxyethylene produced by Union Carbide. The foaming agent, (e.g., polyoxyethylene) may be present in an amount of from 0.1% to 50%, in one embodiment from 0.5% to 20% and in another embodiment from 1% to 10%, or from 2% to 5% by weight of the oral care compositions of the present disclosure.

Surfactants:

The compositions useful in the compositions of the present disclosure may contain anionic surfactants, for example:

i. water-soluble salts of higher fatty acid monoglyceride monosulfates, such as the sodium salt of the monosulfated monoglyceride of hydrogenated coconut oil fatty acids such as sodium N-methyl N-cocoyl taurate, sodium cocomonoglyceride sulfate, ii. higher alkyl sulfates, such as sodium lauryl sulfate, iii. higher alkyl-ether sulfates, e.g., of formula $CH_3(CH_2)_mCH_2(OCH_2CH_2)_nOSO_3X$, wherein m is 6-16, e.g., 10, n is 1-6, e.g., 2, 3 or 4, and X is Na or K, for example sodium laureth-2 sulfate ($CH_3(CH_2)_{10}CH_2(OCH_2CH_2)_2OSO_3Na$), iv. higher alkyl aryl sulfonates such as sodium dodecyl benzene sulfonate (sodium lauryl benzene sulfonate), v. higher alkyl sulfoacetates, such as sodium lauryl sulfoacetate (dodecyl sodium sulfoacetate), higher fatty acid esters of 1,2 dihydroxy propane sulfonate, sulfocolaurate (N-2-ethyl laurate potassium sulfoacetamide) and sodium lauryl sarcosinate.

By "higher alkyl" is meant, e.g., $C_{6-30}$ alkyl. In certain embodiments, the anionic surfactants useful herein include the water-soluble salts of alkyl sulfates having from 10 to 18 carbon atoms in the alkyl radical and the water-soluble salts of sulfonated monoglycerides of fatty acids having from 10 to 18 carbon atoms. Sodium lauryl sulfate, sodium lauroyl sarcosinate and sodium coconut monoglyceride sulfonates are examples of anionic surfactants of this type. In particular embodiments, the anionic surfactant is selected from sodium lauryl sulfate and sodium ether lauryl sulfate. In a particular embodiment, the compositions of the disclosure comprise sodium lauryl sulfate. The anionic surfactant may be present in an amount which is effective, e.g., >0.01% by weight of the formulation, but not at a concentration which would be irritating to the oral tissue, e.g., <10%, and optimal concentrations depend on the particular formulation and the particular surfactant. In one embodiment, the anionic surfactant is present in a toothpaste at from 0.3% to 4.5% by weight, e.g., about 1.5%. The compositions of the disclosure may optionally contain mixtures of surfactants, e.g., comprising anionic surfactants and other surfactants that may be anionic, cationic, zwitterionic or nonionic. Generally, suitable surfactants are those which are reasonably stable throughout a wide pH range. Surfactants are described more fully, for example, in U.S. Pat. No. 3,959,458, to Agricola et al.; U.S. Pat. No. 3,937,807, to Haefele; and U.S. Pat. No. 4,051,234, to Gieske et al, the disclosures of which are incorporated herein by reference in their entireties.

The surfactant or mixtures of compatible surfactants that are included in addition to the anionic surfactants can be present in the compositions of the present disclosure in from 0.1% to 5.0%, in another embodiment from 0.3% to 3.0% and in another embodiment from 0.5% to 2.0% by weight of the total composition. These ranges do not include the anionic surfactant amounts.

In some embodiments, the compositions of the present disclosure include a zwitterionic surfactant, for example a betaine surfactant, for example cocamidopropylbetaine, e.g. in an amount of from 0.1% to 4.5% by weight, e.g. from 0.5 to 2% by weight cocamidopropylbetaine.

Tartar Control Agents:

In various embodiments of the present disclosure, the compositions comprise an anticalculus (tartar control) agent. Suitable anticalculus agents include, without limitation, phosphates and polyphosphates (for example pyrophosphates and tripolyphosphates), polyaminopropanesulfonic acid (AMPS), hexametaphosphate salts, zinc citrate trihydrate, polypeptides, polyolefin sulfonates, polyolefin phosphates, and diphosphonates. The compositions of the disclosure thus may comprise phosphate salts in addition to the zinc phosphate. In particular embodiments, these salts are alkali phosphate salts, e.g., salts of alkali metal hydroxides or alkaline earth hydroxides, for example, sodium, potassium or calcium salts. "Phosphate" as used herein encompasses orally acceptable mono- and polyphosphates, for example, $P_{1-6}$ phosphates, for example monomeric phosphates such as monobasic, dibasic or tribasic phosphate; and dimeric phosphates such as pyrophosphates; and multimeric phosphates, such as tripolyphosphates, tetraphosphates, hexaphosphates and hexametaphosphates (e.g., sodium hexametaphosphate). In particular examples, the selected phosphate is selected from alkali dibasic phosphate and alkali pyrophosphate salts, e.g., selected from sodium phosphate dibasic, potassium phosphate dibasic, dicalcium phosphate dihydrate, calcium pyrophosphate, tetrasodium pyrophosphate, tetrapotassium pyrophosphate, sodium tripolyphosphate, and mixtures of any of two or more of these. In a particular embodiment, for example the compositions may comprise tetrasodium pyrophosphate in an amount of from 0.5 to 5% by weight, e.g., 1-3%, or 1-2% or about 2% by weight of the composition. In another embodiment, the compositions may comprise a mixture of tetrasodium pyrophosphate (TSPP) and sodium tripolyphosphate (STPP), e.g., in proportions of TSPP at from 0.5 to 5 wt. %, such as from 1 to 2 wt. % and STPP at from 0.5% to 6 wt. %, such as 1 to 4%, or 2 to 3% by weight of the composition. Such phosphates are provided in an amount effective to reduce erosion of the enamel, to aid in cleaning the teeth, and/or to reduce tartar buildup on the teeth, for example in an amount of from 0.2 to 20 wt. %, e.g., from 1 to 15 wt. %, by weight of the composition.

Flavoring Agents:

The oral care compositions of the disclosure may also include a flavoring agent. Flavoring agents which are used in the practice of the present disclosure include, but are not limited to, essential oils as well as various flavoring aldehydes, esters, alcohols, and similar materials. Examples of the essential oils include oils of spearmint, peppermint, wintergreen, sassafras, clove, sage, eucalyptus, marjoram, cinnamon, lemon, lime, grapefruit, and orange. Also useful are such chemicals as menthol, carvone, and anethole. Certain embodiments employ the oils of peppermint and spearmint. The flavoring agent may be incorporated in the oral composition at a concentration of from 0.1 to 5% by weight e.g., from 0.5 to 1.5% by weight.

Polymers:

The oral care compositions of the disclosure may also include additional polymers to adjust the viscosity of the formulation or enhance the solubility of other ingredients. Such additional polymers include polyethylene glycols, polysaccharides (e.g., cellulose derivatives, for example carboxymethyl cellulose, hydroxymethyl cellulose, ethyl cellylose, microcrystalline cellulose or polysaccharide gums, for example xanthan gum, guar gum or carrageenan gum). Acidic polymers, for example polyacrylate gels, may be provided in the form of their free acids or partially or fully neutralized water soluble alkali metal (e.g., potassium and sodium) or ammonium salts. In one embodiment, the oral care composition may contain PVP. PVP generally refers to a polymer containing vinylpyrrolidone (also referred to as N-vinylpyrrolidone, N-vinyl-2-pyrrolidione and N-vinyl-2-pyrrolidinone) as a monomeric unit. The monomeric unit consists of a polar imide group, four non-polar methylene groups and a non-polar methane group.

In some embodiments, the compositions of the disclosure comprise one or more polyethylene glycols, for example, polyethylene glycols in a molecular weight range from 200 to 800. For example, the compositions may comprise one or more of polyethylene glycol 200, polyethylene glycol 300, polyethylene glycol 400, polyethylene glycol, 600 or polyethylene glycol 800.

Silica thickeners, which form polymeric structures or gels in aqueous media, may be present. Note that these silica thickeners are physically and functionally distinct from the particulate silica abrasives also present in the compositions, as the silica thickeners are very finely divided and provide little or no abrasive action. Other thickening agents are carboxyvinyl polymers, carrageenan, hydroxyethyl cellulose and water soluble salts of cellulose ethers such as sodium carboxymethyl cellulose and sodium carboxymethyl hydroxyethyl cellulose. Natural gums such as karaya, gum arabic, and gum tragacanth can also be incorporated. Colloidal magnesium aluminum silicate can also be used as component of the thickening composition to further improve the composition's texture. In certain embodiments, thickening agents in an amount of from 0.5% to 5.0% by weight of the total composition are used.

In some embodiments, the compositions of the disclosure may include an anionic polymer, for example in an amount of from 0.05 to 5%. Examples of such agents generally known for use in dentifrice are disclosed in U.S. Pat. Nos. 5,188,821 and 5,192,531, both of which are incorporated herein by reference in their entirety; and include synthetic anionic polymeric polycarboxylates, such as 1:4 to 4:1 copolymers of maleic anhydride or acid with another polymerizable ethylenically unsaturated monomer, preferably methyl vinyl ether/maleic anhydride having a molecular weight (M.W.) of from 30,000 to 1,000,000, such as from 300,000 to 800,000. These copolymers are available for example as Gantrez, e.g., AN 139 (M.W. 500,000), AN 119 (M.W. 250,000) and preferably S-97 Pharmaceutical Grade (M.W. 700,000) available from ISP Technologies, Inc., Bound Brook, N.J. 08805. The enhancing agents when present are present in amounts ranging from 0.05 to 3% by weight. Other operative polymers include those such as the 1:1 copolymers of maleic anhydride with ethyl acrylate, hydroxyethyl methacrylate, N-vinyl-2-pyrollidone, or ethylene, the latter being available for example as Monsanto EMA No. 1103, M.W. 10,000 and EMA Grade 61, and 1:1 copolymers of acrylic acid with methyl or hydroxyethyl methacrylate, methyl or ethyl acrylate, isobutyl vinyl ether or N-vinyl-2-pyrrolidone. Suitable generally, are polymerized olefinically or ethylenically unsaturated carboxylic acids containing an activated carbon-to-carbon olefinic double bond and at least one carboxyl group, that is, an acid containing an olefinic double bond which readily functions in polymerization because of its presence in the monomer molecule either in the alpha-beta position with respect to a carboxyl group or as part of a terminal methylene grouping. Illustrative of such acids are acrylic, methacrylic, ethacrylic, alpha-chloroacrylic, crotonic, beta-acryloxy propionic, sorbic, alpha-chlorsorbic, cinnamic, beta-styrylacrylic, muconic, itaconic, citraconic, mesaconic, glutaconic, aconitic, alpha-phenylacrylic, 2-benzyl acrylic, 2-cyclohexylacrylic, angelic, umbellic, fumaric, maleic acids and anhydrides. Other different olefinic monomers copolymerizable with such carboxylic monomers include vinylacetate, vinyl chloride, dimethyl maleate and the like. Copolymers contain sufficient carboxylic salt groups for water-solubility. A further class of polymeric agents includes a composition containing homopolymers of substituted acrylamides and/or homopolymers of unsaturated sulfonic acids and salts thereof, in particular where polymers are based on unsaturated sulfonic acids selected from acrylamidoalykane sulfonic acids such as 2-acrylamide 2 methylpropane sulfonic acid having a molecular weight of from 1,000 to 2,000,000. Another useful class of polymeric agents includes polyamino acids containing proportions of anionic surface-active amino acids such as aspartic acid, glutamic acid and phosphoserine, e.g. as disclosed in U.S. Pat. No. 4,866,161, issued to Sikes et al., which is also incorporated herein by reference in its entirety.

In some embodiments, there are no anionic polymers present in the composition. In other embodiments, there may be anionic polymers present, but they do not include copolymers of methyl vinyl ether and maleic acid or anhydride.

Humectants:

Within certain embodiments of the oral compositions, it is also desirable to incorporate a humectant to prevent the composition from hardening upon exposure to air. Certain humectants can also impart desirable sweetness or flavor to dentifrice compositions. Suitable humectants include edible polyhydric alcohols such as glycerin, sorbitol, xylitol, propylene glycol as well as other polyols and mixtures of these humectants. In one embodiment of the disclosure, the principal humectant is one of glycerin, sorbitol or a combination thereof. The humectant may be present at levels of greater than 15 wt. %, such as from 15 wt. % to 55 wt. %, or from 20 wt. % to 50 wt. %, or from 20 wt. % to 40 wt. %, or about 20% or about 30% or about 40%, based on the total weight of the composition.

Other Optional Ingredients:

In addition to the above-described components, the embodiments of this disclosure can contain a variety of optional oral care ingredients some of which are described below. Optional ingredients include, for example, but are not limited to, adhesives, sudsing agents, flavoring agents, sweetening agents such as sodium saccharin, additional antiplaque agents, abrasives, aesthetics such as $TiO_2$ coated mica or other coloring agents, such as dyes and/or pigments.

In some embodiments, the compositions of the present disclosure can have any pH suitable for in a product for use in oral care. Examples of suitable pH ranges are from 6 to 9, such as from 6.5 to 8, or 6.5 to 7.5, or about 7.0.

In some embodiments, the oral care compositions of the present disclosure are either essentially free of, free of, or do not include any sodium hexametaphosphate. In some embodiments, the oral care compositions of the present disclosure are either essentially free of, free of, or do not include any halogenated diphenyl ethers (e.g., triclosan).

By "essentially free" is meant that the compositions have no more than 0.01% by weight of these compounds.

In some embodiments, the compositions of the present disclosure are either essentially free of, free of or do not include any complexing agents for increasing solubility of zinc phosphate and/or for maintaining the stannous fluoride in solution. Examples of known complexing agents that can be excluded from the compositions of the present disclosure include the chelating agents taught in U.S. Patent Application No. 2007/0025928, the disclosure of which is hereby incorporated by reference in its entirety. Such chelating agents include mineral surface-active agents, including mineral surface-active agents that are polymeric and/or polyelectrolytes and that are selected from phosphorylated polymers, wherein if the phosphorylated polymer is a polyphosphate, the polyphosphate has average chain length of 3.5 or more, such as 4 or more; polyphosphonates; polycarboxylates; carboxy-substituted polymers; copolymers of phosphate- or phosphonate-containing monomers or polymers with ethylenically unsaturated monomers, amino acids, proteins, polypeptides, polysaccharides, poly(acrylate), poly(acrylamide), poly(methacrylate), poly(ethacrylate), poly(hydroxyalkylmethacrylate), poly(vinyl alcohol), poly(maleic anhydride), poly(maleate) poly(amide), poly (ethylene amine), poly(ethylene glycol), poly(propylene glycol), poly(vinyl acetate) and poly(vinyl benzyl chloride); and mixtures thereof. Other known complexing agents that can be excluded from the compositions of the present disclosure include those taught in CA 2634758, the disclosure of which is incorporated here by reference in its entirety. Examples include polyphosphorylated inositol compounds such as phytic acid, myo-inositol pentakis(dihydrogen phosphate); myo-inositol tetrakis(dihydrogen phosphate), myo-inositol trikis(dihydrogen phosphate), and alkali metal, alkaline earth metal or ammonium salts of any of the above inositol compounds. Phytic acid is also known as myo-inositol 1,2,3,4,5,6-hexakis (dihydrogen phosphate) or inositol hexaphosphoric acid.

In another aspect, the present disclosure provides a method of treatment or prevention of erosive tooth demineralization, gingivitis, plaque, and/or dental caries, the method comprising the application to the oral cavity of a person in need thereof a composition according to the invention (e.g., Composition 1.0 et seq), e.g., by brushing, for example, one or more times per day.

In another aspect, the present disclosure provides a method of using the compositions described herein (e.g., any of Compositions 1.0 et seq) to increase zinc levels in the enamel and to treat, reduce or control the incidence of enamel erosion. The methods comprise applying any of the compositions as described herein to the teeth, e.g., by brushing, or otherwise administering the compositions to the oral cavity of a subject in need thereof. The compositions can be administered regularly, such as, for example, one or more times per day. In various embodiments, administering the compositions of the present disclosure to a patient can provide one or more of the following benefits: (i) reduce hypersensitivity of the teeth, (ii) reduce plaque accumulation, (iii) reduce or inhibit demineralization and promote remineralization of the teeth, (iv) inhibit microbial biofilm formation in the oral cavity, (v) reduce or inhibit gingivitis, (vi) promote healing of sores or cuts in the mouth, (vii) reduce levels of acid producing bacteria, (viii) increase relative levels of non-cariogenic and/or non-plaque forming bacteria, (ix) reduce or inhibit formation of dental caries, (x) reduce, repair or inhibit pre-carious lesions of the enamel, e.g., as detected by quantitative light-induced fluorescence (QLF) or electrical caries measurement (ECM), (xi) treat, relieve or reduce dry mouth, (xii) clean the teeth and oral cavity, (xiii) reduce erosion, (xiv) whiten teeth; (xv) reduce tartar build-up, and/or (xvi) promote systemic health, including cardiovascular health, e.g., by reducing potential for systemic infection via the oral tissues. The disclosure further provides compositions for use in any of the above methods. Further embodiments provide methods wherein at least one tooth is remineralized after administration of a composition as described herein.

The present application further discloses a method of making any of the compositions of the present disclosure. The method comprises combining zinc phosphate and stannous fluoride in water to form an aqueous zinc phosphate mixture. In some embodiments, the zinc phosphate is added to the dentifrice composition as a preformed salt and remains essentially insoluble in the aqueous mixture. The amount of water employed in the mixture can be any of the amounts recited herein for the compositions of the present disclosure. Any standard mixing techniques can be employed to combine the ingredients and form a stable composition without the need for additional complexing agents to solubilize the stannous fluoride, such as any of the above disclosed complexing or chelating agents, or the use of anhydrous mixing techniques such as dissolving stannous fluoride in an anhydrous material such as glycerin.

EXAMPLES

Examples 1 and 2 below look at the amount of water soluble zinc and stannous using flame atomic absorption spectrophotometry (FAAS). All samples (F, Sn, and Zn) are diluted in water, initially, and then subject to accelerated aging over the course of 13 weeks, at either 25° C. or 40° C. This method is based on the principle that water soluble Zn can be measured in oral care products by FAAS after dilution of sample in water. With respect to Sn, a portion of oral care product is digested with an acid mixture (acid soluble tin) or dispersed with water (water soluble tin). Solutions are transferred to a volumetric flask, diluted to volume with water and centrifuged. Tin is detected in the supernatant by atomic absorption spectroscopy and quantitated by comparing the absorbance of the sample solution to absorbances of external calibration standards of known tin concentration.

Additionally, Examples 1 and 2 below use gradient elution ion chromatograph, incorporating conductivity detection, to assay fluoride. Samples are prepared as aqueous slurries followed by centrifugation and dilution. The working solutions are analyzed by gradient ion chromatography with suppressed conductivity detection. Analyte concentrations are determined by relating the component peak areas to corresponding areas of external calibration standards.

Example 1: Stannous Stability with Arginine and Citrate Buffer (*ZnP is Meant to Denote Zinc Phosphate Throughout the Specification and Examples)

TABLE 1

|   | F (Initial) (ppm) | F 13 Wk* (25° C., 40° C.) (ppm) | Sn (Initial) % sol | Sn 13 wk* (25° C., 40° C.) % sol | Zn (Initial) % sol | Zn 13 Wk* (25° C., 40° C.) % sol |
|---|---|---|---|---|---|---|
| SnF, + ZnP + Arg | 1127 | 1136, 1111 | 0.14 | 0.05, 0.05 | 0.28 | 0.26, 0.26 |
| SnF, + ZnP + 1.2 Buffer | 1196 | 1068, 969 | 0.2 | 0.18, 0.15 | 0.31 | 0.25, 0.21 |
| SnF, + ZnP + Arg + 1.2 Buffer (Composition A) | 1134 | 1063, 967 | 0.18 | 0.11, 0.10 | 0.27 | 0.31, 0.27 |
| SnF, + ZnP + Arg + 2.4 Buffer (Composition B) | 1141 | 1067, 1011 | 0.23 | 0.15, 0.13 | 0.34 | 0.43, 0.23 |
| SnF, + ZnP + Arg + 3.6 Buffer (Composition C) | 1197 | 1069, 963 | 0.26 | 0.2, 0.17 | 0.38 | 0.51, 0.47 |

*Values at 13 weeks listed on top are aged at 25° C., values at 13 weeks listed on the bottom are aged at 40° C.

The citrate buffer was tested for its ability to stabilize stannous ions in combination with arginine. Ion concentration was measured over the course of 13 weeks. Formulations with the organic acid buffer system retained a higher percentage of stannous ions than the comparative formulation which did not comprise the organic acid buffer system. The organic acid buffer described above in Compositions A-C contains trisodium citrate dihydrate and citric acid in combination with arginine. Amounts of the buffer are listed as a percentage by weight of the composition.

Formulations with SnZp and Arginine (w/o any citrate buffer) retained only about 36% of the original stannous ion concentration by week 13. Corresponding formulations that contain SnZp, Arginine, and Buffer (1.2%, 2.4%, and 3.6%) were able to retain much more of the original stannous concentration at room temperature ((25 C)): about 61% (at 1.2% buffer), about 65% (at 2.4% buffer) and about 65% (at 3.6% buffer).

Example 2: Stannous Stability with Lysine and Citrate Buffer

TABLE 2

| Description | Aging Time pt | Initial % Sol. Tin | Aged % Sol. Tin | Initial % Sol. Zn | Aged % Sol. Zinc | Initial % F (ppm) | Aged % Sol. F (ppm) |
|---|---|---|---|---|---|---|---|
| SnF + 2.35% ZnP, 1.5% Lysine 1.2% Buffer (Composition D) | Initial 25 C. | 0.25 | | 0.21 | | 1112 | |
| | 4 wks (25 C./40 C.) | | 0.17/0.14 | | 0.25/0.24 | | 1106/1064 |
| | 8 wks (25 C./40 C.) | | 0.19/0.17 | | 0.27/0.25 | | 1059/986 |
| | 13 wks (25 C./40 C.) | | 0.15/0.13 | | 0.25/0.24 | | |
| SnF + 2.35 % ZnP, 1.5% Lysine 2.4.% Buffer (Composition E) | | 0.21 | | 0.26 | | 1081 | |
| | 4 wks (25 C./40 C.) | | 0.23/0.20 | | 0.36/0.34 | | 1098/1027 |
| | 8 wks | | 0.28/0.25 | | 0.41/0.31 | 1033/938 | |
| | 13 wks | | 0.21/0.18 | | 0.35/0.34 | | |
| SnF + 2.35% ZnP, 1.5% Lysine, 3.6% Buffer (Composition F) | | 0.3 | | 0.48 | | 1056 | |
| | 4 wks (25 C./40 C.) | | 0.31/0.26 | | 0.49/0.41 | | 1066/1002 |
| | 8 wks | | 0.32/0.29 | | 0.42/0.48 | 1048/906 | |
| | 13 wks | | 0.26/0.24 | | 0.47/0.44 | | |

The citrate buffer was tested for its ability to stabilize stannous ions in combination with lysine. Ion concentration was measured over the course of 13 weeks. The organic acid buffer described above in Compositions D-F contains trisodium citrate dihydrate and citric acid in combination with arginine. Amounts of the buffer are listed as a percentage by weight of the composition.

Example 3: Zinc Uptake in Bovine Teeth Assays

The three dentifrice composition shown above were compared in a stannous and zinc ion uptake experiments using bovine enamel.

Metal ion uptake is measured using the ESCA technique (X-ray photoelectron spectroscopy). Bovine enamel specimens are used to prepare 3 mm wide disks of bovine enamel in which all but the exposed enamel surface is protected with acrylic resin. Each enamel sample is etched with 1M perchloric acid solution, and then rinsed. 2 mL of fresh human saliva is then added, and the samples are incubated at 37° C. for 2 hours in order to cause pellicle formation. After removing the saliva and rinsing, the samples are treated with 2 mL of a 1:2 slurry of test composition in distilled water for 2 minutes at 37° C. with shaking. One sample is treated with water as a negative control to determine baseline metal ion content. After rinsing the samples with water, they are submitted to ESCA analysis. The baseline metal ion levels measured in the negative control are subtracted from the other test measurements to determine metal ion uptake from the dentifrice compositions. The results are shown in Table 3 below.

Test Formulations with Dentifrice Formulation:

Test Formulation A: SnF+2.35% ZnP, 1.5% Lysine, 1.2% Buffer

Test Formulation B: SnF+2.35% ZnP, 1.5% Lysine, 2.4% Buffer

Test Formulation C: SnF+2.35% ZnP, 1.5% Lysine, 3.6% Buffer

Control Formulations contain: 0.454% SnF, and 2.5% zinc lactate.

The results demonstrate improved metal deposition of zinc, in in vitro bovine uptake assays when compared to control formulations which contain 0.454% SnF and 2.5% zinc lactate, but which do not contain zinc phosphate:

TABLE 3

|  | Relative Increase in Metal Deposition: Zinc (ppm)* |
| --- | --- |
| Test Formulation A | 1.7 |
| Test Formulation B | 2.0 |
| Test Formulation C | 2.1 |
| Control Formulation | 1 |

*Values are normalized to control and show increase of zinc deposition relative to control Table 4 demonstrates the buffer composition used in above Examples 1-3.

TABLE 4

|  | Buffer System (wt %) | |
| --- | --- | --- |
| Test Comp. | Sodium Citrate* | Citric Acid |
| Test Compositions w/o Buffer | 0.00 | 0.00 |
| Compositions with 1.2% Buffer | 1.0 | 0.2 |
| Compositions with 2.4% Buffer | 2.0 | 0.4 |
| Compositions with 3.6% Buffer | 3.0 | 0.6 |

The water concentration of the above formulations is between 17.0% to 21.0% by wt. These are considered "high water" formulations. Therefore, the Applicants have addressed the instability of stannous ions without having to resort to either a.) low water formulations; or b.) dual phase compositions.

Experimental dentifrice compositions used to observe stannous ion stability are prepared based on the base formulation shown in Tables 5 and 6. Each dentifrice comprises 0.454% stannous fluoride and 2.35% zinc phosphate hydrate, and arginine 1.5%, but varies in the concentration of citric acid and trisodium citrate dihydrate present—these concentrations are detailed in the above Table 2.

Ingredients of Representative Formulas in Tables 5 and 6 are listed by weight of the composition.

TABLE 5

| Ingredient | Weight % |
| --- | --- |
| Water | Q.S. |
| Humectants (Sorbitol, Glycerin, Propylene Glycol, Polyethylene Glycol) | 40-47 |
| Abrasives | 20 |
| Thickeners | 3.6 |
| Trisodium Citrate, Dihydrate | 0.0-3.0 |
| Zinc Phosphate | 2.35 |
| Flavor, Sweetener, Colors | 0.65 |
| Tetrasodium Pyrophosphate | 2 |
| Anionic Surfactant | 1.5 |
| Microcrystalline Cellulose/ Sodium CMC NF | 0.5-1.5 |
| Zwitterionic Surfactant | 1.25 |
| Citric Acid- Anhydrous | 0.0-3.0 |
| Stannous Fluoride | 0.454 |
| Arginine | 1.50% |
| TOTAL | 100% |

TABLE 6

| Ingredient | Weight % |
| --- | --- |
| Water | Q.S. |
| Humectants (Sorbitol, Glycerin, Propylene Glycol, Polyethylene Glycol) | 40-47 |
| Abrasives | 20 |
| Thickeners | 3.6 |
| Trisodium Citrate, Dihydrate | 0.0-3.0 |
| Zinc Phosphate | 2.35 |
| Flavor, Sweetener, Colors | 0.65 |
| Tetrasodium Pyrophosphate | 2 |
| Anionic Surfactant | 1.5 |
| Microcrystalline Cellulose/ Sodium CMC NF | .5-1.5 |
| Zwitterionic Surfactant | 1.25 |
| Citric Acid-Anhydrous | 0.0-3.0 |
| Stannous Fluoride | 0.454 |
| Lysine | 1.50% |
| TOTAL | 100% |

While the present invention has been described with reference to embodiments, it will be understood by those skilled in the art that various modifications and variations may be made therein without departing from the scope of the present invention as defined by the appended claims.

The invention claimed is:

1. A high water oral care composition, wherein the amount of water is 10% by weight or more, comprising
an orally acceptable carrier,
zinc phosphate wherein the amount of zinc phosphate is present in an amount of from 0.05 to 10% by weight, relative to the weight of the oral care composition,
stannous fluoride,
arginine,
and an organic acid buffer system,
wherein the organic buffer system comprises citric acid and a sodium citrate salt, in a weight ratio of from 1:3 to 1:6, and
wherein the organic acid buffer system in an amount of 0.1 to 5.0% by weight of the composition, measured as the combined amount of citric acid and any conjugate base salt.

2. A composition according to claim 1, wherein the zinc phosphate is a preformed salt of zinc phosphate.

3. A composition according to claim 1, wherein the amount of the stannous fluoride is from 0.01% to 5% by weight, relative to the weight of the oral care composition.

4. A composition according to claim 1, wherein the composition comprises arginine at about 1.5% by wt.

5. A composition according to claim 1, further comprising an effective amount of one or more alkali phosphate salts.

6. A composition according to claim 1, wherein the alkali phosphate salts comprise tetrasodium pyrophosphate or tetrapotassium pyrophosphate, optionally in an amount of 0.5 to 5% by weight of the composition.

7. A composition according to claim 1, wherein the alkali phosphate salts comprise sodium tripolyphosphate or potassium tripolyphosphate, optionally in an amount of 0.5 to 6% by weight of the composition.

8. A composition according to claim 1, further comprising one or more sources of zinc ions in addition to the zinc phosphate, for example, a zinc salt selected from zinc citrate, zinc oxide, zinc lactate, zinc pyrophosphate, zinc sulfate, or zinc chloride.

9. A composition according to claim 1, wherein the oral care composition is a dentifrice.

10. A method of treatment or prevention of erosive tooth demineralization, gingivitis, plaque, and/or dental caries, the method comprising the application to the oral cavity of a person in need thereof a composition according to claim 1.

11. A composition of claim 1, wherein the amount of water is 10%-90% by weight.

* * * * *